United States Patent
Delaney et al.

(10) Patent No.: US 11,163,928 B2
(45) Date of Patent: *Nov. 2, 2021

(54) CLASSICAL OPTIMIZER FOR QUANTUM CHEMISTRY CIRCUIT SYNTHESIS

(71) Applicants: IonQ, Inc., College Park, MD (US); Duke University, Durham, NC (US)

(72) Inventors: Conor Delaney, Webster, NY (US); Jungsang Kim, Chapel Hill, NC (US); Yunseong Nam, North Bethesda, MD (US)

(73) Assignees: IonQ, Inc, College Park, MD (US); Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/006,314

(22) Filed: Aug. 28, 2020

(65) Prior Publication Data
US 2020/0394353 A1  Dec. 17, 2020

Related U.S. Application Data

(63) Continuation of application No. 16/213,379, filed on Dec. 7, 2018, now Pat. No. 10,776,544.

(51) Int. Cl.
| | |
|---|---|
| *G06F 30/327* | (2020.01) |
| *G06N 10/00* | (2019.01) |
| *G06F 30/20* | (2020.01) |
| *G06F 111/02* | (2020.01) |

(52) U.S. Cl.
CPC ............ *G06F 30/327* (2020.01); *G06F 30/20* (2020.01); *G06N 10/00* (2019.01); *G06F 2111/02* (2020.01)

(58) Field of Classification Search
CPC .... G06F 30/327; G06F 30/20; G06F 2111/02; G06F 30/30; G06N 10/00; G06N 5/003; G16C 10/00
See application file for complete search history.

(56) References Cited

U.S. PATENT DOCUMENTS

| | | |
|---|---|---|
| 2016/0283857 A1 | 9/2016 | Babbush et al. |
| 2019/0370679 A1 | 12/2019 | Curtis et al. |

OTHER PUBLICATIONS

International Search Report and Written Opinion from International Application No. PCT/US2019/065115 dated Feb. 18, 2020.

*Primary Examiner* — Stacy Whitmore
(74) *Attorney, Agent, or Firm* — Brundidge & Stanger, P.C.

(57) ABSTRACT

A computer-implemented method, system and a computer readable medium storing executable instructions for optimizing a quantum circuit are disclosed. The computer-implemented method includes receiving one or more parameters for simulation of evolution of at least one quantum state of a chemical entity to be simulated; generating a quantum circuit for the simulation; performing one or more operations to minimize quantum resources to be used for the generated quantum circuit based on the one or more parameters; and placing quantum resources among one or more elementary logical units (ELUs) based on any one or more of: frequency of occurrence of the quantum resources in the generated quantum circuit, order of occurrence of the quantum resources in the generated quantum circuit, connectivity parameters between one or more quantum resources, efficiency of gates between specific quantum resources, quality of gates between specific quantum resources or a combination thereof.

39 Claims, 14 Drawing Sheets

FIG. 4A

1. Term Merging $$e^{i[\theta(1\otimes\sigma^+\otimes\sigma^z\otimes\sigma^z)+\phi(1\otimes\sigma^-\otimes\sigma^z\otimes\sigma^z)]}$$

$1 \otimes \sigma^+ \otimes \sigma^z \otimes \sigma^z$ $1 \otimes \sigma^x \otimes \sigma^z \otimes \sigma^z$
$+i\, 1 \otimes \sigma^y \otimes \sigma^z \otimes \sigma^z$ $1 \otimes \sigma^- \otimes \sigma^z \otimes \sigma^z$ $1 \otimes \sigma^x \otimes \sigma^z \otimes \sigma^z$
$-i\, 1 \otimes \sigma^y \otimes \sigma^z \otimes \sigma^z$ $$e^{i[1\otimes\sigma^x\otimes\sigma^z\otimes\sigma^z((\theta+\phi)/2)+1\otimes\sigma^y\otimes\sigma^z\otimes\sigma^z(i(\theta-\phi)/2)]}$$

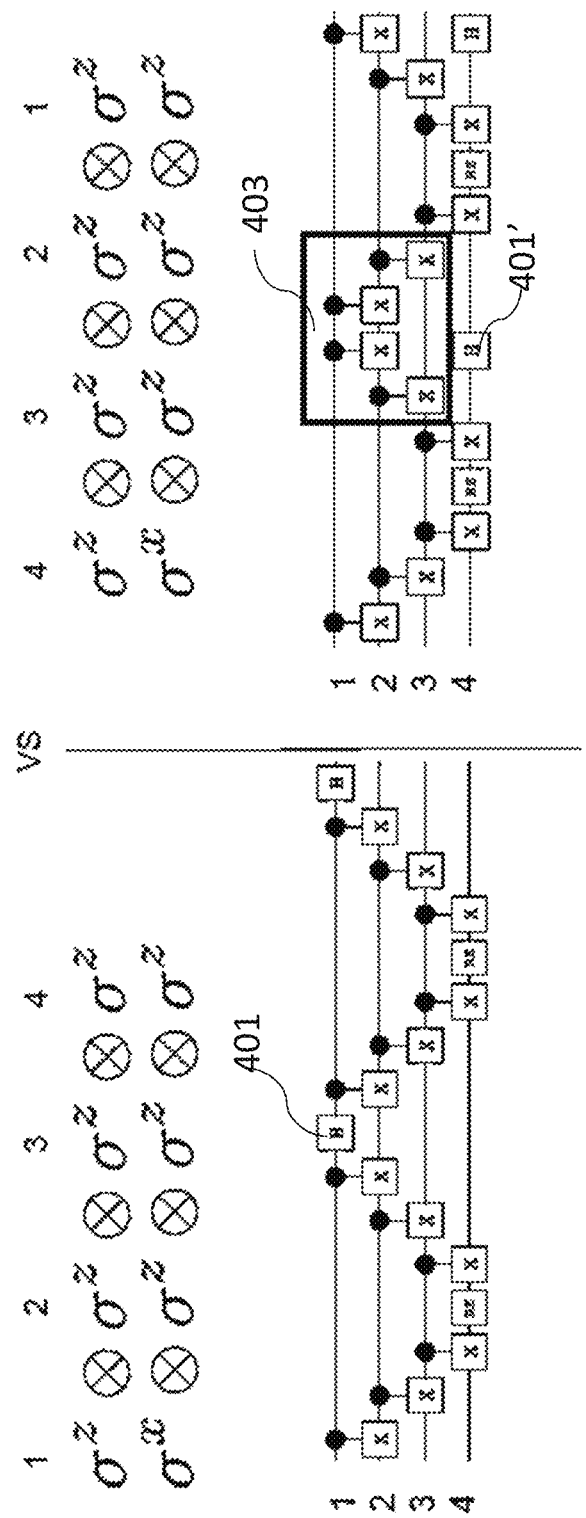

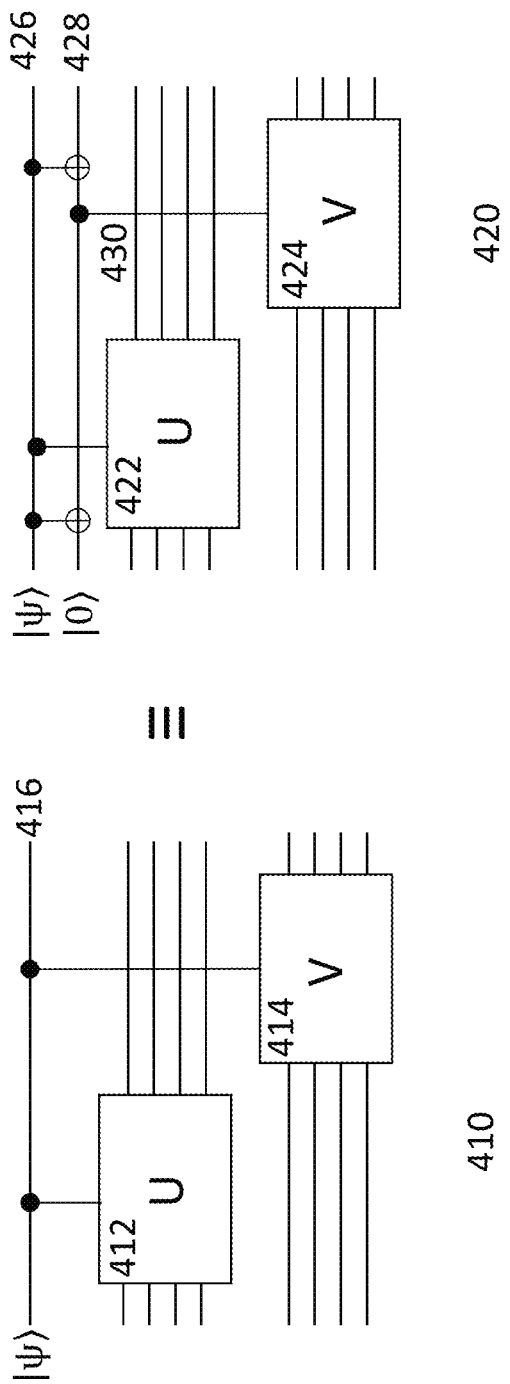

CLASSICAL OPTIMIZER FOR QUANTUM CHEMISTRY CIRCUIT SYNTHESIS

CROSS-REFERENCE TO RELATED APPLICATIONS

This application is a Continuation of U.S. application Ser. No. 16/213,379, filed Dec. 7, 2018, which is incorporated herein by reference by its entirety.

TECHNICAL FIELD

The embodiments described herein pertain generally to generating optimized quantum circuits for simulation of quantum system for a chemical entity.

BACKGROUND

A quantum computer is a computational system which uses quantum-mechanical phenomena, such as superposition and entanglement, to process data. Unlike digital computers, in which data is encoded into binary digits (bits) in one of two definite states ("0" or "1"), quantum computation requires data to be encoded into quantum bits (hereafter "qubits"), for which a single qubit may represent a "1," a "0," or any quantum superposition of the two qubit states. In general, a quantum computer with N qubits may be in an arbitrary superposition of up to 2" different states simultaneously, i.e., a pair of qubits may be in any quantum superposition of four states, and three qubits may be in any superposition of eight states.

Quantum computers are able to solve certain problems much more quickly and efficiently than digital computers (alternatively referred to herein as "classical computers"). In the operation of a quantum computer, computations may be initialized by setting qubits in a controlled initial state. By manipulating those qubits, predetermined sequences of quantum logic gates are realized that represent the solution to a problem to be solved, called a quantum algorithm. Quantum algorithms, such as Shor's algorithm, Simon's algorithm, etc., run faster than any possible probabilistic classical algorithm.

Based on the inherent advantages in quantum computers in solving certain problems, the challenge is in programming quantum computers to take advantage of their strengths in solving those problems.

SUMMARY

In one example embodiment, a computer-implemented method for optimizing a quantum circuit includes receiving one or more parameters for simulation of evolution of at least one quantum state of a chemical entity to be simulated; generating a quantum circuit for simulation of evolution of the at least one quantum state of the chemical entity; performing one or more operations to minimize quantum resources to be used for the generated quantum circuit based on the one or more parameters; and placing quantum resources among one or more elementary logical units (ELUs) based on any one or more of: frequency of occurrence of the quantum resources in the generated quantum circuit, order of occurrence of the quantum resources in the generated quantum circuit, connectivity parameters between one or more quantum resources, efficiency of gates between specific quantum resources, quality of gates between specific quantum resources or a combination thereof.

In another example embodiment, a system for optimizing a quantum circuit comprising at least one processor and a memory wherein the memory stores executable instructions for optimizing a quantum circuit that, upon execution by the processor, cause the processor to perform functions including receiving one or more parameters for simulation of evolution of at least one quantum state of a chemical entity to be simulated; generating a quantum circuit for simulation of evolution of the at least one quantum state of the chemical entity; performing one or more operations to minimize quantum resources to be used for the generated quantum circuit based on the one or more parameters; and placing quantum resources among one or more elementary logical units (ELUs) based on any one or more of: frequency of occurrence of the quantum resources in the generated quantum circuit, order of occurrence of the quantum resources in the generated quantum circuit, connectivity parameters between one or more quantum resources, efficiency of gates between specific quantum resources, quality of gates between specific quantum resources or a combination thereof.

In yet another embodiment, a computer-readable medium storing executable instructions for optimizing a quantum circuit that, upon execution, cause a digital computing processor to perform functions including receiving one or more parameters for simulation of evolution of at least one quantum state of a chemical entity to be simulated; generating a quantum circuit for simulation of evolution of the at least one quantum state of the chemical entity; performing one or more operations to minimize quantum resources to be used for the generated quantum circuit based on the one or more parameters; and placing quantum resources among one or more elementary logical units (ELUs) based on any one or more of: frequency of occurrence of the quantum resources in the generated quantum circuit, order of occurrence of the quantum resources in the generated quantum circuit, connectivity parameters between one or more quantum resources, efficiency of gates between specific quantum resources, quality of gates between specific quantum resources or a combination thereof.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

FIGS. 4A, 4B and 4C show an example processing flow by which at least portions of the method for optimizing a quantum circuit are implemented, in accordance with at least some embodiments described herein;

FIG. 4D shows an example processing flow by which at least portions of the method for optimizing a quantum circuit are implemented, in accordance with at least some embodiments described herein;

DETAILED DESCRIPTION

Figure 1A:
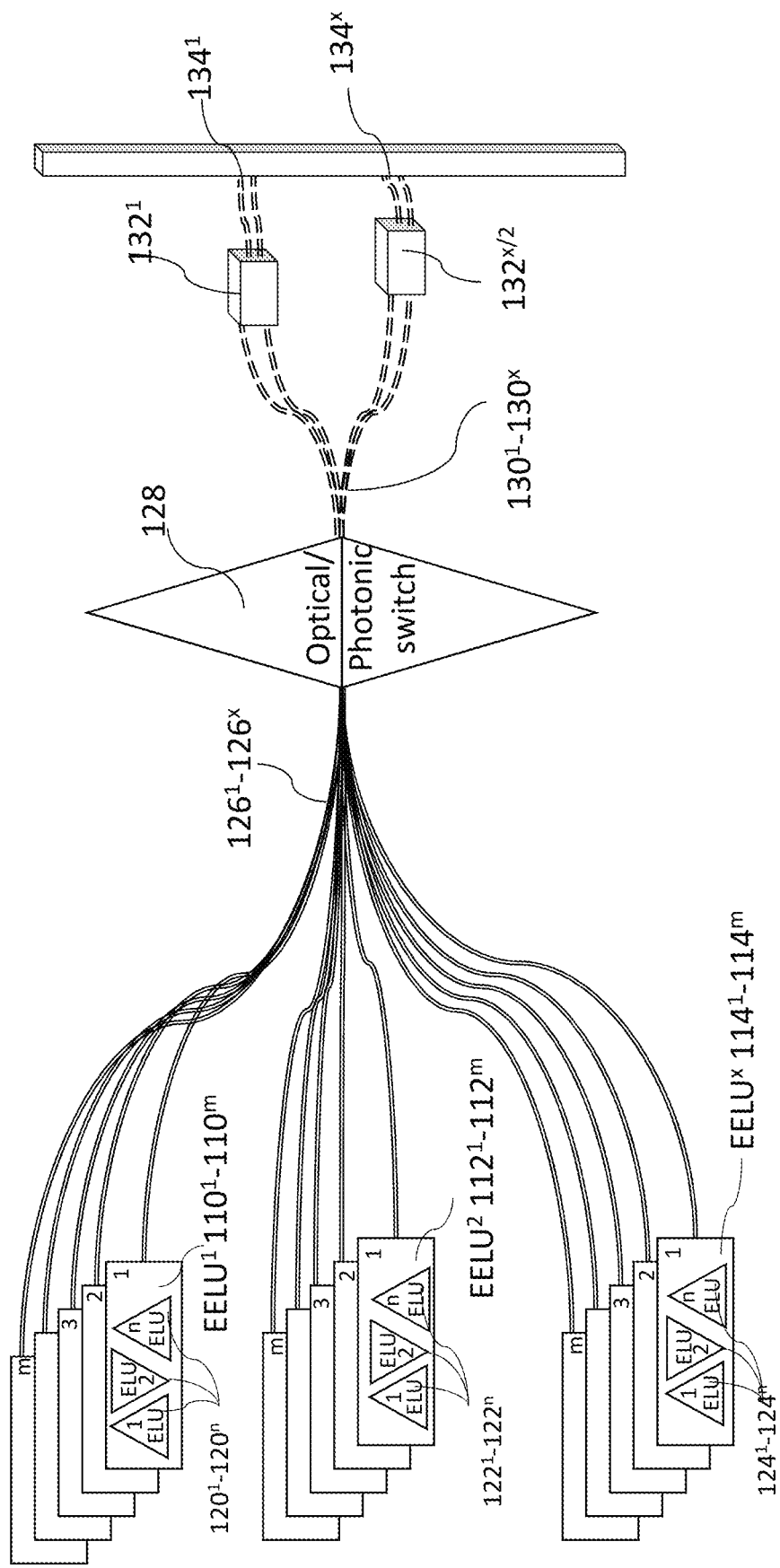
FIG. 1A illustrates a portion of an exemplary quantum system architecture in accordance with at least some embodiments described herein.

In the following detailed description, reference is made to the accompanying drawings, which form a part of the description. In the drawings, similar symbols typically identify similar components, unless context dictates otherwise. Furthermore, unless otherwise noted, the description of each successive drawing may reference features from one or more of the previous drawings to provide clearer context and a more substantive explanation of the current example embodiment. Still, the example embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein and illustrated in the drawings, may be arranged, substituted, combined, separated, and designed in a wide variety of different configurations, all of which are explicitly contemplated herein.

Described herein are approaches embodied in one or more of systems, apparatuses, applications, programs, and methods by which quantum hybrid computation including both classical and quantum computing are securely and efficiently implemented by, e.g., apportioning computing between co-located computing devices in disparate computing environments.

In the present description, the following terms may be used, in addition to their accepted meaning, as follows:

"Classical computing," "classical program," "digital computing," "digital program," or variations thereof may refer to computing/processing of data that has been converted into binary numbers. Classical computing processors may include, but not be limited to, a central processing unit (CPU), a graphical processing unit (GPU), a tensor processing unit (TPU), application-specific integrated circuits (ASICs), field programmable gate arrays, etc., and unbound permutations thereof. Non-limiting examples thereof may include a classical optimization function that may be parallelized and run on a multicore classical computer; a classical computer with a GPU for performing parallel calculations, etc.

"Quantum computing," or variations thereof, may refer to computing/processing of data that has been encoded into qubits. Quantum computing utilizes qubits to perform high-level gating functions to produce results that are faster than classical computing for a specific class of computational problems.

"Environment" may refer to a computing environment in which are found components that when executing program may utilize, e.g., utilities such as libraries, other programs, other hardware, etc. Thus, reference may be made herein to a classical computing environment, a quantum computing environment, etc.

A "circuit" may refer to one or more quantum functions.

In accordance with the example embodiments described herein, quantum computing includes executing iterative processes by which a quantum circuit may be written in a classical computing environment for execution in a quantum computing environment. Non-limiting examples of such classical computing environment that can be used include a desktop computer, a laptop computer, mobile device, etc. The quantum circuit may be submitted via a network, e.g., the Internet, to a quantum computing device at which the quantum circuit may be queued with other quantum circuits, in the same manner as, for example, batch processing for a mainframe computing device. The queued quantum circuits may be executed in turn.

Iterative, or cumulative, results of the computing of the quantum circuit may be received and collated in either the classical computing environment in which the quantum circuit was written or in a different classical computing environment in which the execution of the quantum circuit is managed. Whichever classical computing environment, the quantum circuit may be updated or rewritten based upon results of the most recent iteration or upon cumulative results of the computing up to that point.

Quantum chemistry problems are considered to be one of important applications of quantum computers. The embodiments described herein disclose a method, a system and a computer program product to synthesize efficient quantum circuits that are used to simulate an atom, a molecule and/or an ion evolving according to its particular evolution operator. The evolution operator at a given time $e^{iHt}$ may be derived by using a time dependent or time independent Schrödinger's Equation. The embodiments described herein improve the efficiency of quantum circuits, maximize savings of quantum resources and leverage unique capabilities, such as global gates that offer a more efficient implementation when compared to efficiency offered by usage of local entangling gates. The global gates may be provided by, e.g., ion-trap quantum computers, to further save quantum resources. Other computers that provide global gates may also be used. Quantum resources are defined as quantum bits also known as qubits required for computations.

Figure 1B:
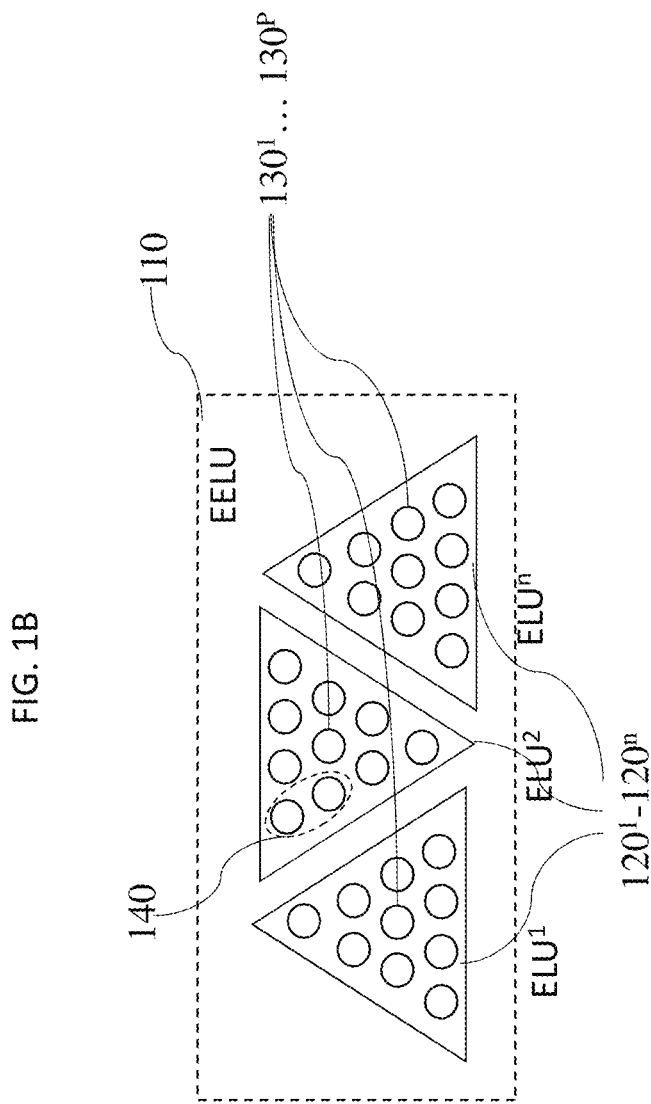
FIG. 1B illustrates an exemplary elementary logic unit of the quantum system architecture in accordance with at least some embodiments described herein.

FIG. 1A illustrates a portion of an exemplary quantum system architecture in accordance with at least some embodiments described herein. As illustrated in FIG. 1A, the exemplary system architecture includes a number of extended elementary logic units (EELUs) $110^1$-$110^n$, $112^1$-$112^n$, $114^1$-$114^n$ . . . etc. Each EELU further includes a number of N-qubit registers, also known as elementary logic units (ELUs) $120^1$-$120^n$, $122^1$-$122^n$, $124^1$-$124^n$ . . . etc., which further include trapped ion qubits as shown in FIG. 1B. Controlling the states of these qubits by applying adequate control signals, for example, via laser beam, to one or more subsets of these qubits, quantum gates between the subset of qubits may be realized. The qubits from different EELUs and ELUs are interconnected or entangled through photonic quantum channels $126^1$-$126^x$ using reconfigurable optical or photonic switch 128. In this approach, a pair of entangled qubits can be generated between two EELUs, where one qubit from the pair resides on each EELU being connected. Such an entangled pair can be generated by an ion from each EELU emitting a single photon whose internal degree of freedom (such as the polarization, frequency, or a position in time) serves as a photonic qubit that is entangled with the ion that is emitting this photon. Two photons emitted by each ion in the two EELUs are brought together at a 50/50 beam splitter $132^1$ . . . $132^{x/2}$, and subsequently detected at the two output ports $134^1$ . . . $134^x$ of the beam splitter. When a specific outcome is achieved (such as each output port of the beam splitter detecting one photon simultaneously), this signals a successful creation of an entangled ion pair between the EELUs. Use of an optical crossconnect switch (or a photonic switch) 128 allows photons from arbitrary pairs of the EELUs in the system to be brought together via photonic quantum channels $126^1$ . . . $126^x$, enabling the generation of entangled ion pairs between an arbitrary pair of EELUs in the system. Once the entangled pair is generated, it can be used as a resource to either teleport a qubit from one of the EELUs to the other (known as quantum teleportation process), or apply two-qubit entangling gate between an ion qubit in one EELU and another ion qubit in the other EELU (known as teleporting a gate).

FIG. 1B illustrates an exemplary elementary logic unit of the quantum system architecture in accordance with at least some embodiments described herein. As illustrated in FIG. 1A, exemplary system architecture includes a number of extended elementary logic units (EELUs), for example, 110. As illustrated in FIG. 1B, each EELU further includes a number of registers, also known as elementary logic units (ELUs) $120^1$-$120^n$, which further include trapped ion qubits $130^1$-$130^P$ referred to as trapped ions or qubits and also as quantum resources. Controlling the states of these qubits $130^1$-$130^P$ by applying adequate control signal, for example, via laser beam, to one or more subsets of these qubits $130^1$-$130^P$ quantum gates between the subset of qubits $130^1$-$130^P$ may be realized via local Coulomb interactions between qubits 140. The number of trapped ions in an ELU may change over time, as trapped ions are shuttled from one ELU to another to realize quantum functions.

Details of the scalable quantum system architecture described in FIGS. 1A and 1B are provided in U.S. Pat. No. 9,858,531 entitled "FAULT TOLERANT SCALABLE MODULAR QUANTUM COMPUTER ARCHITECTURE WITH AN ENHANCED CONTROL OF MULTI-MODE COUPLINGS BETWEEN TRAPPED ION QUBITS".

In one example embodiment, a computer-implemented method for optimizing a quantum circuit includes receiving one or more parameters for simulation of evolution of at least one quantum state of a chemical entity to be simulated; generating a quantum circuit for simulation of evolution of the at least one quantum state of the chemical entity; performing one or more operations to minimize quantum resources to be used for the generated quantum circuit based on the one or more parameters; and placing quantum resources among one or more elementary logical units (ELUs) based on any one or more of: frequency of occurrence of the quantum resources in the generated quantum circuit, order of occurrence of the quantum resources in the generated quantum circuit, connectivity parameters between one or more quantum resources, efficiency of gates between specific quantum resources, quality of gates between specific quantum resources or a combination thereof.

The computer-implemented method for optimizing a quantum circuit includes receiving one or more parameters for simulation of evolution of at least one quantum state of a chemical entity to be simulated; deriving a time evolution operator $e^{iHt}$ for the chemical entity, wherein deriving evolution operator for the chemical entity further comprises: deriving fermionic Hamiltonian for the chemical entity, and transforming fermionic Hamiltonian to a qubit Hamiltonian using one or more transformation algorithms, wherein the one or more transformation algorithm comprises any one or more of: Jordan-Wigner transformation, Parity transformation and Bravyi-Kitaev transformation. The method further includes converting the derived evolution operator to an evolution operator for a quantum computer to be used for simulation of the evolution of the at least one quantum state according to the evolution operator and the one or more parameters; and generating a quantum circuit for simulation of the quantum system for the chemical entity, which is optimized by performing one or more operations to minimize quantum resources to be used for the generated quantum circuit based on the one or more parameters; and placing quantum resources among one or more elementary logical units (ELUs) based on any one or more of: frequency of occurrence of the quantum resources in the generated quantum circuit, order of occurrence of the quantum resources in the generated quantum circuit, connectivity parameters between one or more quantum resources, efficiency of gates between specific quantum resources, quality of gates between specific quantum resources or a combination thereof.

The computer-implemented method, system and computer-readable medium storing executable instructions for optimizing a quantum circuit are described in detail below and illustrated in accompanying figures.

Figure 2A:
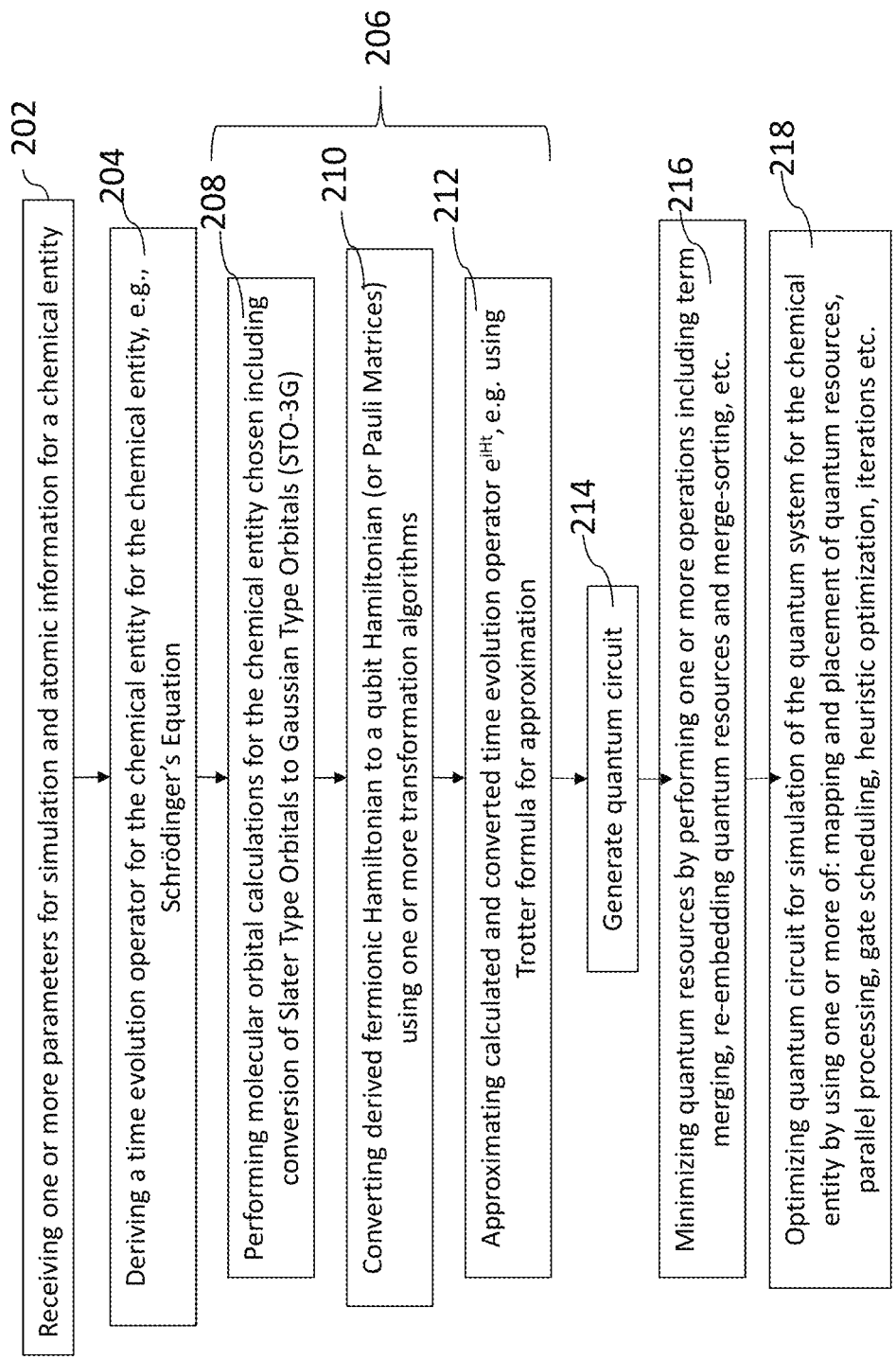
FIGS. 2A and 2B show an example processing flow by which at least portions of the method for optimizing a quantum circuit are implemented, in accordance with at least some embodiments described herein.
Figure 2B:
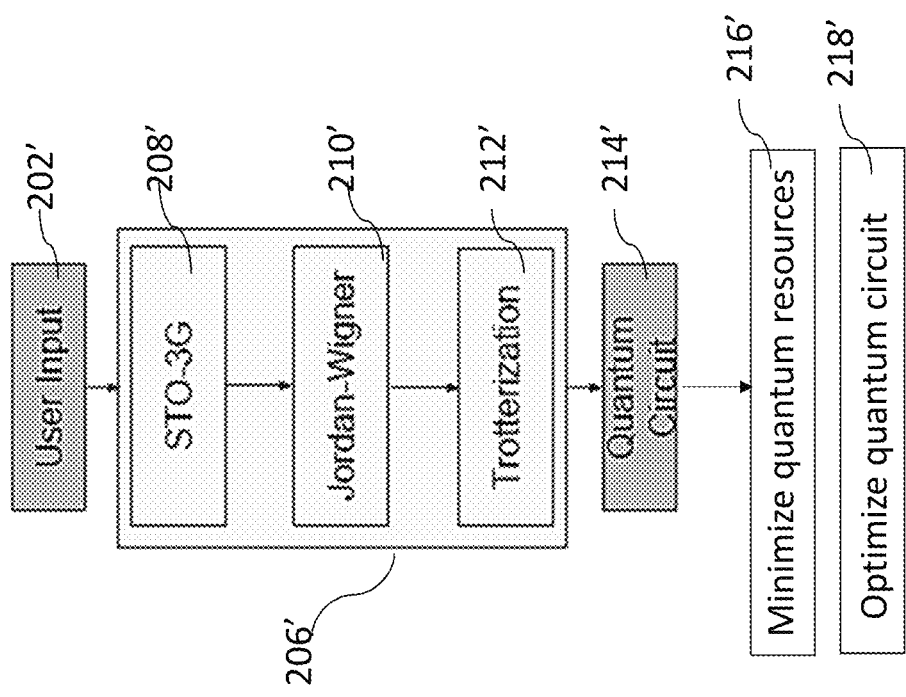

FIG. 2A and FIG. 2B illustrate at least some portions of an exemplary method for optimizing a quantum circuit, the method includes receiving one or more parameters for simulation of evolution of at least one quantum state of a chemical entity to be simulated via step 202. The one or more parameters for simulation of evolution of the at least one quantum state of the chemical entity include optimization parameters, wherein the optimization parameters include any one or more of: an error tolerance for the quantum circuit, a number of gates permitted for the quantum circuit, a number of qubits permitted for the quantum circuit; and atomic information for the chemical entity including atomic coordinates and atomic number etc. The molecular orbital calculations are performed for the chemical entity chosen, e.g., conversion of Slater Type Orbitals to Gaussian Type Orbitals (STO-3G) is performed via step 208 as depicted in FIG. 2A and via step 208' as depicted in FIG. 2B. These calculations further involve deriving evolution operator $e^{iHt}$ for the chemical entity from Schrödinger's Equation via step 204.

In an embodiment, the evolution operator for the chemical entity is derived from Schrödinger's Equation, which may be time dependent or time independent, where is a wave function for electron system for the chemical entity, His a Hamiltonian operator and E is energy of the electron for the electron system for the chemical entity. The evolution operator $e^{iHt}$ may be derived from time independent Schrödinger's Equation: $\hat{H}\psi = E\psi$;

or time dependent Schrödinger's Equation:

$$i\hbar \frac{\partial}{\partial t} |\Psi(r, t)\rangle = \hat{H}|\Psi(r, t)\rangle$$

The Hamiltonian coefficient or overlap integral calculated by the one or more of the above-mentioned methods, e.g., using the Schrödinger's Equation, for the chemical entity, is known as a fermionic Hamiltonian. For example, numerical values of the coefficient $h_{pq}$ and $h_{pqrs}$ based on the chosen chemical basis for a chemical entity, e.g., a molecule, may be calculated using an equation:

$$\hat{\mathcal{H}} = \sum_{p,q} h_{pq} f_p^\dagger f_q + \sum_{p,q,r,s} h_{pqrs} f_p^\dagger f_q^\dagger f_r f_s$$

Wherein $f^\dagger \equiv$ Creation operator, and f Annihilation operator; and wherein the first term represents kinetic energy plus electron-core interaction and the second term represents electron-electron interaction; and wherein Overlap Integrals are represented as:

$$h_{pq} = \int d\vec{r}\, \chi_p^*(\vec{r}) \left( \hat{T} + \sum_{nuc} \hat{V}_{nuc} \right) \chi_q(\vec{r})$$

$$h_{pqrs} = \int d\vec{r}_1 d\vec{r}_2 \frac{\chi_p^*(\vec{r}_1)\chi_q^*(\vec{r}_2)\chi_r(\vec{r}_2)\chi_s(\vec{r}_1)}{r_{12}}$$

$\chi(\vec{r}) \equiv$ Orbital

Slater type orbitals (STO) → Gaussian type orbitals (GTO)

The numerical values of the coefficient $h_{pq}$ and $h_{pqrs}$ based on the chosen chemical basis thus computed are stored in a memory and used further for conversion from natural basis to qubit basis. The processor may be provided with rules to decide which chemical basis to choose based on atomic information, e.g., coordinates, atomic numbers, and optimization parameters and hardware constraints, e.g., an error tolerance for the quantum circuit, a number of gates permitted for the quantum circuit, a number of qubits permitted for the quantum circuit, connectivity parameters between the qubits, speed, efficiency and quality of gates between specific pairs (or sets) of qubits in the system, etc. provided.

The generation of the optimized quantum circuit for simulation of the quantum system for the chemical entity, which may be an atom, a molecule or an ion, includes choosing a chemical basis. Although embodiments of the system and process described herein are explained using an exemplary chemical basis STO-3G for hydrogen-like atom since it is the simplest minimal basis set, other chemical bases may also be chosen.

The chemical basis chosen comprises atomic orbitals, e.g., Gaussian-type orbitals, Slater-type orbitals, or numerical atomic orbital. The chemical entity for which the chemical basis is chosen may be as simple as hydrogen atom (one basis function for minimal chemical basis) or may be any other complex molecule or ion for which atomic information/parameters, e.g., coordinates, atomic numbers is known and may be provided as user input. The user input may also include hardware constraints along with optimization parameters, e.g., error rate of each quantum gate, error tolerance for the quantum circuit, number of qubits available in the hardware, connectivity between the qubits, maximum number of gates permitted for the quantum circuit, maximum number of qubits permitted for the quantum circuit, and maximum duration of time allowed for the simulation, etc. Other constraints may also be provided.

The Hamiltonian of interest includes the Hamiltonian coefficients h's, which entail the information about the energy of the system written in some chemical basis, e.g., a hydrogenic-like slater-type orbital basis. If this orbital is then approximated using three Gaussian functions (STO-3G), Hamiltonian coefficients h may be explicitly calculated. Hydrogenic-like slater-type orbital basis is chosen here as an example only and other bases may also be used, similarly, STO-3G is chosen here as an example, since it is a minimal basis, however, other combinations of functions may also be used, as described above.

The derived fermionic Hamiltonian thus obtained is then converted to a qubit Hamiltonian using one or more transformation algorithms via step 206 as depicted in FIG. 2A and via step 210' as depicted in FIG. 2B. The transformation algorithm used for such transformation may include any one or more of: Jordan-Wigner transformation, Parity transformation and Bravyi-Kitaev transformation. Other suitable transformation algorithms, or a combination of more than one transformation methods, may also be used. For example, Jordan-Wigner transformation, which may be represented by the following equation:

$$\hat{\mathcal{H}} = \sum_{p,q} h_{pq} f_p^\dagger f_q + \sum_{p,q,r,s} h_{pqrs} f_p^\dagger f_q^\dagger f_r f_s$$

$$\downarrow$$

$$\hat{\mathcal{H}} = \sum_{p,q} h_{pq} a_p^\dagger a_q + \sum_{p,q,r,s} h_{pqrs} a_p^\dagger a_q^\dagger a_r a_s$$

The calculated and converted time evolution operator $e^{iHt}$ is then approximated using Trotter formula for approximation via step 206 as depicted in FIG. 2A and via step 212' as depicted in FIG. 2B. Other suitable methods for approximation may also be used, e.g., algorithms based on high-order product formulas (PFs), direct application of the Taylor series (TS), quantum signal processing method (QSP) etc. The choice of approximation parameters depends on optimization parameters including any one or more of: error tolerance for the quantum circuit, number of gates permitted for the quantum circuit, number of qubits permitted for the quantum circuit etc. The optimization parameters may also include minimization of number of quantum resources used in the generated quantum circuit so as to minimize errors, as use of more quantum resources may induce more errors. The Trotter formula used to approximate the time evolution of the quantum system, or used to create the variational trial wavefunction (also known as the ansatz function) may be represented as follows:

$$\exp\left(-it \sum_{j=1}^{L} \alpha_j H_j\right) \approx [S_{2k}(\lambda)]^r$$

-continued $$S_2(\lambda) := \prod_{j=1}^{L} \exp(\alpha_j H_j \lambda / 2) \prod_{j=L}^{1} \exp(\alpha_j H_j \lambda / 2)$$

$$S_{2k}(\lambda) := [S_{2k-2}(p_k\lambda)]^2 S_{2k-2}((1-4p_k)\lambda)[S_{2k-2}(p_k\lambda)]^2$$

Wherein the first order formula may be represented as $$e^{i(A+B)\epsilon} = 1 + i(A+B)\epsilon - (A^2 + AB + BA + B^2)\epsilon^2/2 + \ldots$$

$$e^{iA\epsilon}e^{iB\epsilon} = 1 + i(A+B)\epsilon - (A^2 + 2AB + B^2)\epsilon^2/2 + \ldots$$

→ Match up to first order

And $2k^{th}$ order formula may be represented as:

$$\exp\left(-it\sum_{j=1}^{L}\alpha_j H_j\right) = \exp\left(\lambda\sum_{j=1}^{L}\alpha_j H_j\right)^r \approx \prod_{j=1}^{L}[\exp(\alpha_j H_j \lambda)]^r$$

The approximated evolution operator thus obtained and the calculated Hamiltonian coefficient for the chemical entity under consideration for the simulation are then used as an input to the circuit synthesis toolkit to generate a generic circuit that simulates the quantum system for the chemical entity via step 214 and 216' as depicted in FIGS. 2A and 2B respectively. The generated quantum circuit is then optimized by using one or more of: mapping and placement of quantum resources, parallel processing, scheduling, and using heuristic optimization, etc. and is further illustrated in FIGS. 3A, 3B, 4A, 4B, 4C, 4D, 4E and 4F, and description accompanying FIGS. 3A, 3B, 4A, 4B, 4C, 4E and 4F.

Quantum chemistry calculations are very complex and hence require a large number of quantum resources for a quantum computer to perform those computations. As discussed above in the description accompanying FIG. 1A and FIG. 1B, exemplary system architecture includes a number of extended elementary logic units (EELUs). Each EELU further includes a number of registers, also known as elementary logic units (ELUs), which further include trapped ion qubits. Controlling the states of these qubits by applying adequate control signal, for example, via laser beam, to one or more subsets of these qubits, quantum gates between the subset of qubits may be realized via local Coulomb interactions between qubits. The qubits from different EELUs and ELUs are interconnected or entangled through photonic quantum channels using reconfigurable optical or photonic switch.

Therefore, the resources may be arranged within different ELUs based on the frequency of appearance due to different levels of connectivity for qubits that are within the same ELU; for qubits that are within different ELUs but within the same EELU; and for qubits that are within different EELUs. For example, the elementary logic units (ELUs) shown in FIG. 1A and FIG. 1B include a number of qubits. It is difficult to grow the ELUs beyond certain number of qubits, for example 30 qubits per ELU and still maintain connectivity among the qubits included in that ELU. One of the ways to overcome this issue is by creating more ELUs with a certain number of qubits, for example ten ELUs per one EELU, where each ELU includes, for example, 30 qubits, and providing connections between different ELUs. The number of qubits illustrated here are for example only and a smaller or larger number of qubits per ELU may be used to allow for a technically feasible and efficient system. Also, the number of qubits in each ELU and the number of ELUs in each EELU may not be all identical: one can imagine ELUs with different numbers of qubits in each ELU, or EELUs with different number of ELUs in each EELU. Furthermore, the number of qubits in each ELU and the number of ELUs in each EELU can be dynamically reconfigured by software control, e.g., the number of quantum resources in each ELU, the number of ELUs in each EELU and the number of EELUs used in the computations can be varied over the duration of the computation. The gate operation between the qubits included in the single ELU are simpler than the gate operations between the qubits from different ELUs, since it involves moving a subset of qubits from one ELU to another ELU. However, since the EELUs reside on a chip, there are limitations as to the number of ELUs that can be accommodated within a single EELU. Therefore, a number of EELUs, each with a number ELUs contained within them, are manufactured. The photonic or optical switch network shown in FIG. 1A allows the connection between one or more qubits from one EELU with one or more qubits from another EELU, forming pairs of entangled qubits between the EELUs, as required to perform the quantum circuit operations. The process of connecting a qubit from one EELU with a qubit from another EELU is also known as teleportation (of either qubits or gates), which in this case is achieved via generating shared entangled pairs of qubits, rather than physical movement of qubits which is done when a qubit from one ELU is entangled with a qubit from another ELU within the same EELU.

Since the qubits within the ELU are very well connected, qubits from different ELUs on the same EELU are well connected and qubits from different EELUs are somewhat connected, it is important to arrange or map the qubits in an efficient way to accommodate specific circuit blocks that show up in the quantum chemistry calculations based on the frequency of appearance/occurrence of qubits within that circuit block. The placement of qubits may additionally or alternatively be based on the sequence of appearance of qubit gates among them to accommodate specific circuit blocks that show up in the quantum chemistry calculations. The process of placing of specific qubits on specific ELUs based on frequency of appearance and/or order of appearance can be automated using a software tool, that takes into account the constraints of the underlying quantum computer hardware.

Additionally, the qubits where maximum interaction is required to perform quantum operations may be placed close to each other, for example, within a single ELU and close to each other within the single ELU, thereby saving gates utilized for connecting the two qubits that are placed next to or close to each other. This may result in placement of other qubits far from each other, however, since connecting the qubits that are placed far from each other may be required fewer times, even though that connection may require more time or other resources like more quantum logic gates, it will still result in overall smaller number of gates being used and thus utilization of less quantum resources or reduced execution time. The methods for optimization via efficient mapping and placement of quantum resources using different techniques is described herein and also illustrated by example circuits shown in FIGS. 3A, 3B, 4A, 4B, 4C, 4D, 4E and 4F, and described in detail in the description accompanying FIGS. 3A, 3B, 4A, 4B, 4C, 4D, 4E and 4F.

Due to inherent limitation as to number of qubits that can be accommodated within a single ELU and number of ELUs that can be accommodated within a single EELU, additional optimization using other techniques such as but not limited to scheduling as well as parallel processing and storing the results of the parallel processing may also be employed. For example, different computations may be performed on different EELUs in parallel and the results may be stored until they are required for further processing. Quantum teleportation process is discussed in U.S. Pat. No. 9,858,531 and discussed above in the description accompanying FIGS. 1A and 1B, may be used to carry out communication between the parallelly processed computations. For example, the various terms in the Trotter formula can in practice be re-ordered and executed while keeping the errors within the allowed bound. If there are several terms in the Trotter formula that do not involve overlapping qubits, their order can be shifted without any penalties. Therefore, each group of terms in the Trotter formula that do not share common qubits between the groups can be mapped on to a single ELU (or EELU), and the operations can be executed in parallel. Then, those terms that share common qubits between the groups can be executed, by exercising communication mechanism of qubits between ELUs (such as shuttling of ion qubits) or between EELUs (such as photonic interconnect) which are connected by a qubit communication bus. Such methods for optimization via mapping and placement of qubits, parallel processing, gate scheduling and teleporting are illustrated by FIGS. 3A, 3B, 4D, 4E and 4F and described in detail in the description accompanying FIGS. 3A, 3B, 4D, 4E and 4F.

The generic circuit generated for chosen chemical basis as illustrated in FIGS. 2A and 2B and described in the description accompanying FIGS. 2A and 2B is thus mapped to generate quantum circuit via step 214 as illustrated in FIG. 2A and 214' as illustrated in FIG. 2B where the quantum resources used in the quantum circuits are optimized or minimized via step 216 as illustrated in FIG. 2A and 216' as illustrated in FIG. 2B. This optimization or minimization of quantum resources is further illustrated in FIGS. 4A, 4B and 4C and described in detail in descriptions accompanying FIGS. 4A, 4B and 4C.

The quantum circuit for simulation of the quantum system for the chemical entity is then further optimized by using different techniques including any one or more of: mapping and placement of quantum resources, parallel processing, gate scheduling, heuristic optimization, etc. via step 218 as illustrated in FIG. 2A and 218' as illustrated in FIG. 2B. This further optimization of quantum circuit using mapping and placement of quantum resources, parallel processing and gate scheduling is further illustrated in FIGS. 3A, 3B, 4D, 4E and 4F and described in detail in descriptions accompanying FIGS. 3A, 3B, 4D, 4E and 4F.

The quantum resources for optimization of the quantum circuit may include any one or more of: quantum computations used for simulation which may further include number of qubits used in a circuit block as well as number of quantum gates, error tolerance for the quantum circuit and time taken to provide results of the simulation. The optimized quantum circuit thus produced may provide time evolution of the chosen chemical entity which may not be limited to a short-term evolution, for example, timescales corresponding to establishment of the steady-state energy spectrum, but rather over an extended period of time, such as the timescales corresponding to propagation of an excitation above the ground-state of the energy of the system, or the timescale to control external parameters to force the time-evolution of the system (such as in adiabatic time evolution of a quantum system).

The core of circuit optimization lies in revealing the repeated pattern of Pauli string prefix in the individual qubit-Hamiltonian terms represented in the Pauli-matrix basis that may arise from the transformation of the physical-level Hamiltonian. For example, for typical chemistry problems, the Wigner-Jordan transformation represents the fermion creation operator $\hat{a}_j$ and the annihilation operator $\hat{a}_j^\dagger$ in the Pauli Matrix basis are represented as:

$\hat{a}_j = \mathbb{I} \otimes^{j-1} \otimes \hat{\sigma}_- \otimes \hat{\sigma}_z^{N-j-1}$ $\hat{a}_j^\dagger = \mathbb{I} \otimes^{j-1} \otimes \hat{\sigma}_+ \otimes \hat{\sigma}_z^{N-j-1}$ Using this transformation and noting that $\hat{\sigma}_\pm = \hat{\sigma}_x \pm i\hat{\sigma}_y$, the terms in the Hamiltonian of the chemical entity, $h_{ji}\hat{a}_j^\dagger \hat{a}_i$ or $h_{jirs}\hat{a}_j^\dagger \hat{a}_r^\dagger \hat{a}_i \hat{a}_s$, will be expressed as a product of Pauli operators. In general, the products of two or four $\sigma_\pm$'s lead to a two- or four-fold product of $\hat{\sigma}_x$ and $\hat{\sigma}_y$ operators corresponding to the electron occupation in the molecular orbital represented by the qubit, accompanied by a series of $\hat{\sigma}_z$ operators "connecting" the terms that involve the $\hat{\sigma}_x$ and $\hat{\sigma}_y$ operators to reflect the proper anti-symmetry of the electron-electron exchange. This series of $\hat{\sigma}_z$ operators is often referred to as the Jordan-Wigner strings.

Figure 3A:
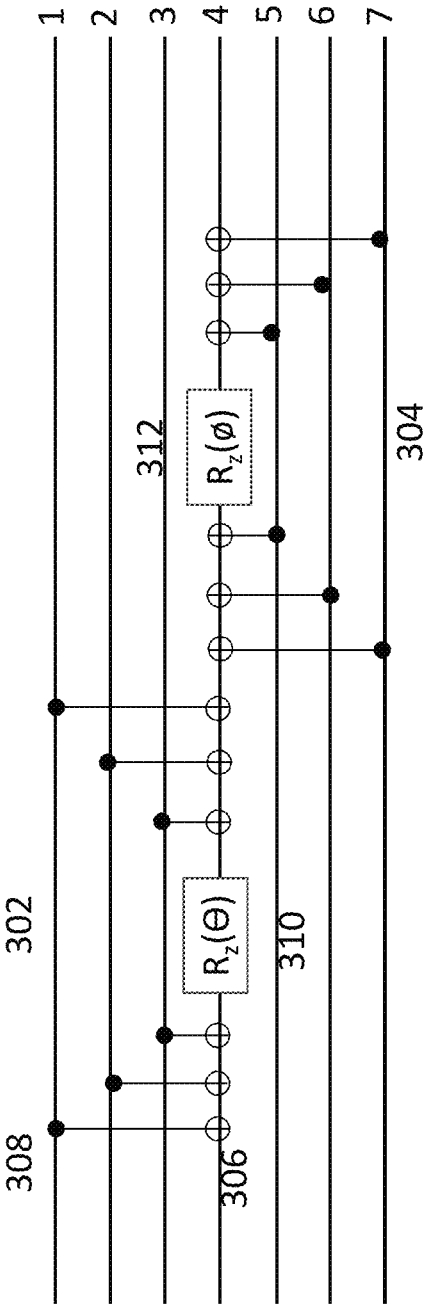
FIGS. 3A and 3B show different methods for performing gate operations using quantum circuit, in accordance with at least some embodiments described herein.
Figure 3B:
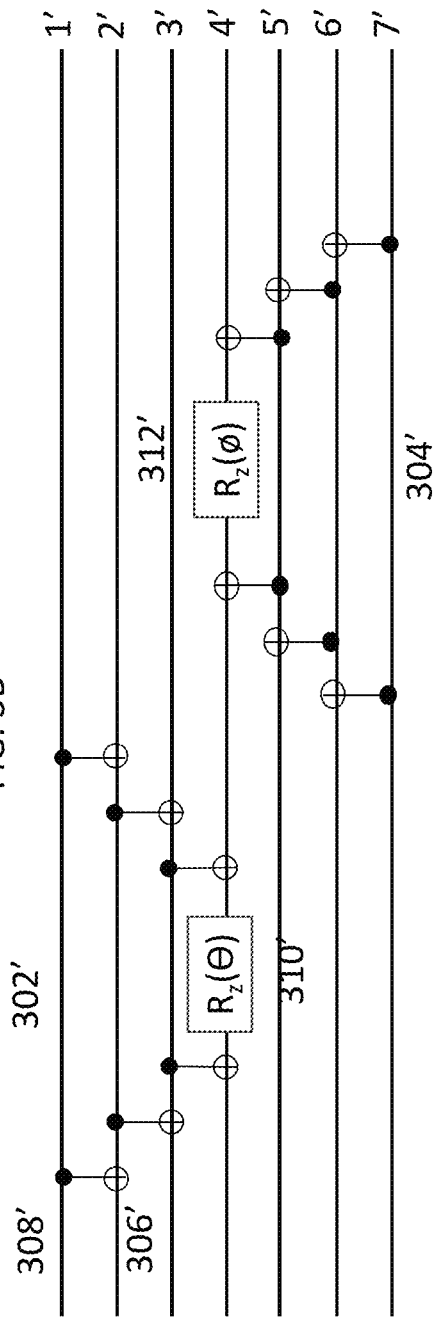

Thus, for solving chemistry problems by performing operations using quantum circuit, connections between certain qubits may be required. FIGS. 3A and 3B show two different (yet equivalent) methods of implementing representative circuits corresponding to two terms of the Hamiltonian in the Trotter expansion, for example, FIG. 3A shows one term 302 involving qubits 1, 2, 3 and 4, followed by another term 304 involving qubits 4, 5, 6 and 7, similarly, FIG. 3B shows one term 302' involving qubits 1', 2', 3' and 4', followed by another term 304' involving qubits 4', 5', 6' and 7'. Although 7 qubits are shown here as an example, the person skilled in the art may readily recognize that a smaller or larger number of qubits may be used.

The method shown FIG. 3A shows the implementation of the four-product Pauli matrices using a series of controlled-NOT (CNOT) gates each connecting two qubits (where the target qubit, e.g., 306 denoted by ⊕ is flipped between $|0\rangle$ and $|1\rangle$ if and only if the control qubit, e.g., 308, denoted by the filled dot, is in the $|1\rangle$ state), followed by shifting the relative phase of the $4^{th}$ qubit by the angle θ (denoted by $R_z(\theta)$ 310, where the phase of the $|1\rangle$ state is shifted by $e^{i\theta}$ relative to the $|0\rangle$ state), followed by the inverse sequence of the CNOTs applied earlier in the sequence. In this circuit, the CNOT gates in the series are applied between arbitrary pair of qubits in the system, and share a common target qubit 306. This is referred to as a "jump-type" implementation of the Hamiltonian evolution. In the presence of Jordan-Wigner strings, the sequence of the CNOT gates can be significantly longer.

FIG. 3B represents an alternative way of implementing the circuit corresponding to the time evolution due to the same Hamiltonian term. The method shown FIG. 3B shows the implementation of the four-product Pauli matrices using a series of controlled-NOT (CNOT) gates each connecting two qubits (where the target qubit, e.g., 306' denoted by ⊕ is flipped between $|0\rangle$ and $|1\rangle$ if and only if the control qubit, e.g., 308', denoted by the filled dot, is in the $|1\rangle$ state), followed by shifting the relative phase of the $4^{th}$ qubit by the angle θ (denoted by $R_z(\theta)$ 310', where the phase of the $|1\rangle$ state is shifted by $e^{i\theta}$ relative to the $|0\rangle$ state), followed by the inverse sequence of the CNOTs applied earlier in the sequence. In this method, the CNOT gate sequences are applied in series between nearest-neighbor qubits. This is referred to as a "step-type" implementation of the Hamiltonian evolution.

Two identical CNOT gates applied back-to-back leaves the initial state to be the same as the final state. In that sense, application of two CNOT gates back-to-back is equivalent to doing nothing at all, and so two CNOT gates cancel each other out if they are applied back-to-back. Proper scheduling of gates may result in more instances of gate cancellations and hence minimization of quantum resources leading to error minimization. Gate scheduling is a process by which the sequence of quantum logic gates that constitute the quantum computation process, for example, for a chemistry calculation, is applied to the qubits once they are placed onto the physical qubits in the quantum computer hardware. The circuits shown in FIGS. 3A and 3B are examples of scheduling of gates on qubits that are assigned or mapped to represent the electron populations for molecular orbits. Optimized gate scheduling can lead to better circuit performance, due to gate cancellations and/or parallel processing.

For computing the properties of a complex chemical entity, the time evolution due to a large number of Hamiltonian terms have to be simulated using the Trotter expansion. By carefully ordering the Hamiltonian terms in the Trotter expansion, many of the Jordan-Wigner strings can be cancelled out. The process of mapping of specific qubits representing the molecular orbitals in the Hamiltonian to physical qubits in an ELU on the quantum computer is known as qubit mapping. In order to take advantage of the full connectivity within an ELU, the Hamiltonian terms in the Trotter expansion may be divided into groups, where each group contains many of the qubits that are used repetitively in those terms, and assign them on to the physical qubits in a single ELU. The efficient mapping of specific qubits representing the molecular orbitals in the Hamiltonian to physical qubits and efficient placement of physical qubits (qubits) allows for the simulations in each group to be started in parallel in each ELU or EELU. There inevitably are qubits that are shared between different groups: these qubits are placed in one ELU first, and once all the simulations involving that qubit is completed in the group, it may be either shuttled to another ELU in the same EELU, or teleported to the proper ELU in another EELU, so that further simulation involving this qubit in a different group may continue. The shuttling of qubits from one ELU to another ELU within the same EELU provides a connection between the different ELUs of the same EELU via a qubit communication bus. In order to minimize the communication costs between ELUs and EELUs, the placing of the qubits to the ions in the ELUs are done in such a way that the number of shuttling between ELUs within the same EELU and teleportation between EELUs are minimized. Thus, mapping and placing of quantum resources or qubits among one or more elementary logical units (ELUs) is based on any one or more of: frequency of occurrence of the quantum resources in the generated quantum circuit, order of occurrence of the quantum resources in the generated quantum circuit, connectivity parameters between one or more quantum resources, efficiency of gates between specific quantum resources, quality of gates between specific quantum resources, etc.

Figure 4C:
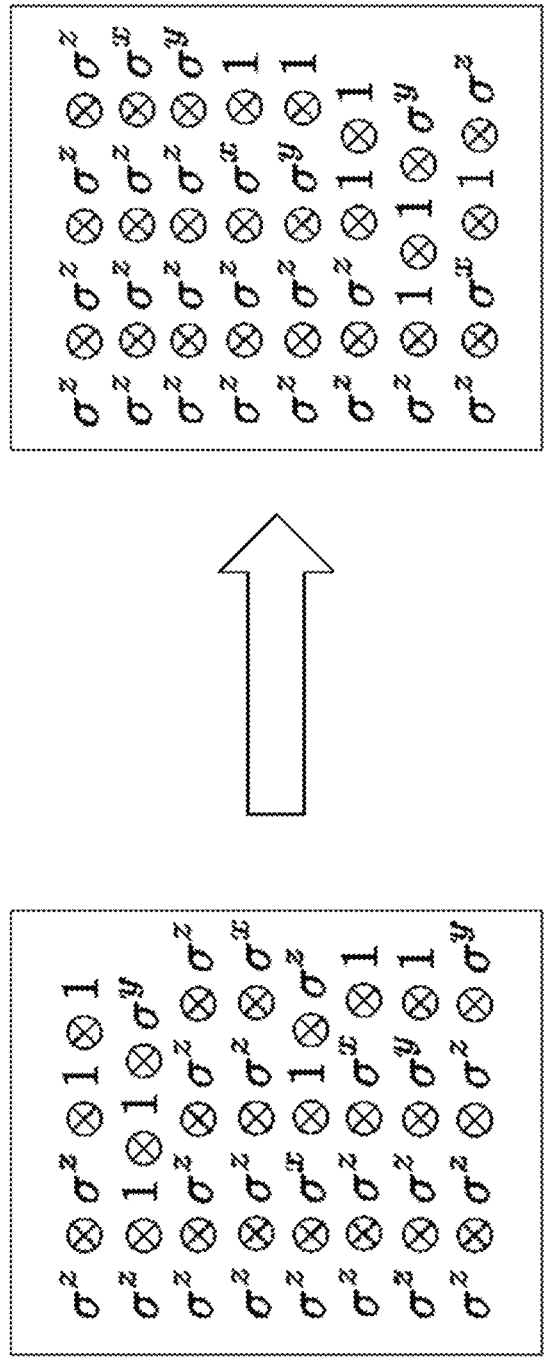

Various circuit optimization techniques may be used to reduce the number of gates needed to implement the Hamiltonian evolution. FIGS. 4A, 4B and 4C show example processing flows by which at least portions of the method for optimizing a quantum circuit are implemented, in accordance with at least some embodiments described herein, e.g., different steps involved in Heuristic optimization. For example, FIG. 4A illustrates term merging, wherein two Hamiltonian terms with identical Pauli products may be combined into a single term. FIG. 4B illustrates an exemplary qubit re-embedding technique: the two Hamiltonian terms in this example, namely $\hat{\sigma}_z\hat{\sigma}_z\hat{\sigma}_z\hat{\sigma}_z$ and $\hat{\sigma}_x\hat{\sigma}_z\hat{\sigma}_z\hat{\sigma}_z$, utilize two similar "step-type" implementation of each Trotter term. Simply by labeling the qubits differently so that the Hadamard (H) gate 401' in between the two terms is applied to the same qubit on which the $R_z(\theta)$ gate is applied, four CNOT gates 403 may be eliminated in the process. FIG. 4C illustrates an exemplary merge-sorting process, where the terms in the Trotter expansion are ordered so that the number of basis changes among the Pauli matrices ($\hat{I}$, $\hat{\sigma}_x$, $\hat{\sigma}_y$, and $\hat{\sigma}_z$) between the subsequent terms is minimized (usually reduced to one or two). In this case, many of the CNOT gates in the implementation of each Trotter term cancels out between neighboring terms, using either the "jump-type" or "step-type" implementation of the terms. Using the "jump-type" implementation results in more cancellations of the CNOT gates than the "step-type" implementation when the basis for two of the four terms are changed between $\hat{\sigma}_x$ and $\hat{\sigma}_y$.

FIG. 4D shows an example processing flow by which at least portions of the method for optimizing a quantum circuit are implemented, in accordance with at least some embodiments described herein. As discussed above, due to inherent limitation as to number of qubits that can be accommodated within a single ELU and number of ELUs that can be accommodated within a single EELU, additional optimization using other techniques such as but not limited to qubit mapping, placement of qubits, gate scheduling as well as parallel processing and storing the results of the parallel processing for later use may also be employed. For example, when using Trotter-Suzuki approximation where repetitive calculations have to be performed, which may be represented as:

$$e^{i(H_0+H_1+H_2\ldots)t} \cong (e^{iH_0t/n}e^{iH_1t/n}e^{iH_2t/n}e^{iH_3t/n}\ldots)^n$$

FIG. 4D illustrates an example of using an extra qubit to parallelize the circuit execution. In the example 410, a common qubit 416 is used for two different controlled operations, for example, controlled-U 412 and controlled-V 414. While all other qubits associated with operation U 412 and operation V 414 are independent, the sharing of common control qubit 416 prohibits scheduling and executing the two operations operation U 412 and operation V 414 in parallel. In the example 420, an entangled pair, for example, 426 and 428, for operation U 422 and for operation V 424 of control qubits, is created with the CNOT gate, and each qubit in the entangled pair is allowed to control the operation U 422 and operation V 424. At the end of the controlled-U 422 and controlled-V 424 process, another CNOT gate for the pair of control qubits may be used to restore the initial state of the control qubits (not shown). Although the two figures are equivalent, in 410, the two controlled operations (controlled-U 412 and controlled-V 414) can be scheduled to run in parallel, as they involve completely independent set of qubits, that is do not share a common qubit.

Figure 4E:
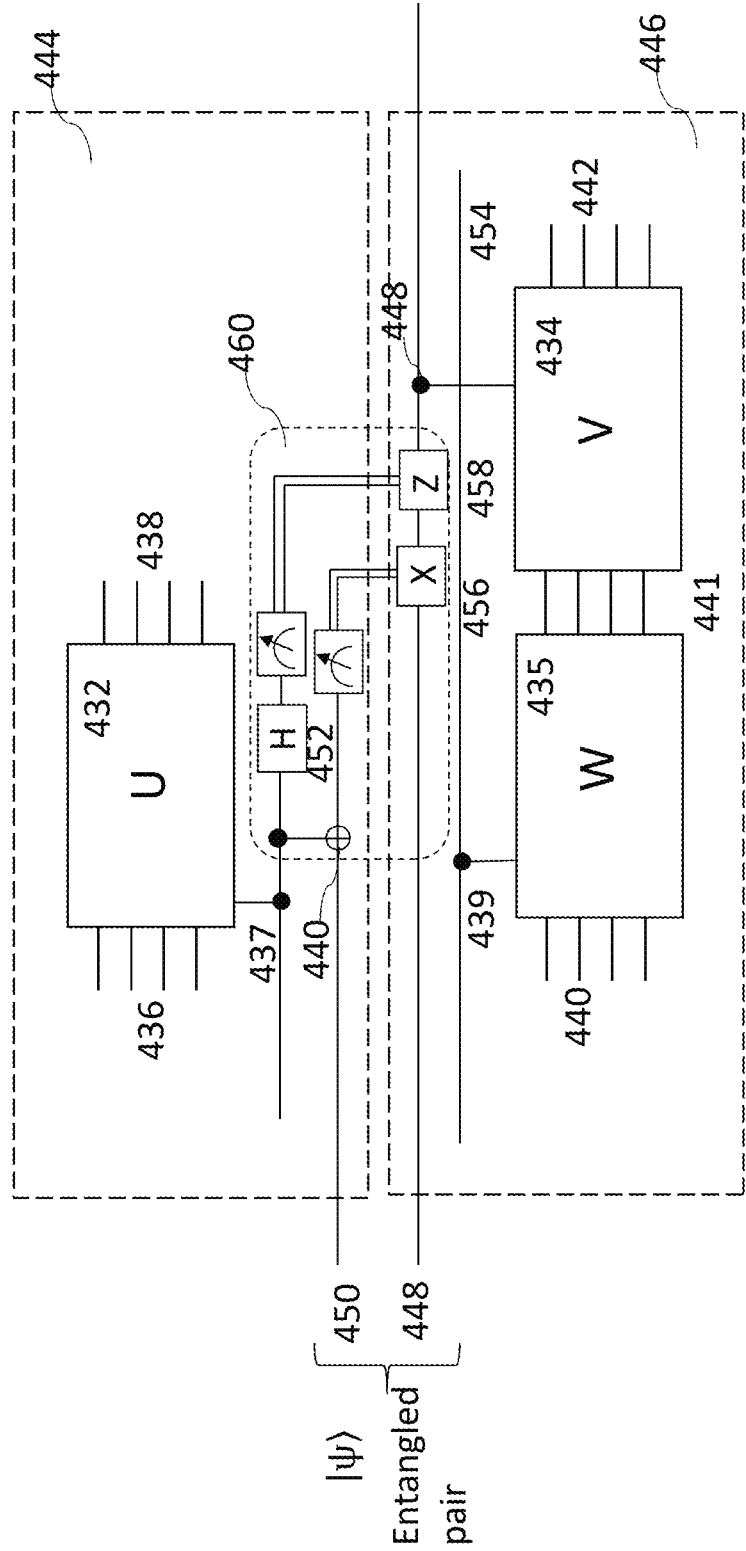
FIG. 4E shows an example processing flow by which at least portions of the method for optimizing a quantum circuit are implemented, in accordance with at least some embodiments described herein.

FIG. 4E shows an example of parallel processing as well as scheduling the gate execution, where different computations may be performed on different EELUs, 444 and 446, in parallel and the results may be stored until they are required for further processing. In this example, one qubit must be shared between the quantum circuits carried out on EELU 444 and the quantum circuit carried out on EELU 446. This shared qubit is first mapped to qubit 437 placed in EELU 444, and the unitary operation U 432 controlled by this qubit 437 is carried out. After that, the qubit 437 must be teleported to EELU 446 for further processing of controlled-V operation 434 involving qubits in EELU 446. This is accommodated by an entangled pair |ψ>, established between a qubit 450 in EELU 444 and a qubit 448 in EELU 446, through the photonic network. This entangled pair can be established at any time before the qubit teleportation is needed. Upon completion of the controlled-U operation 432 in EELU 444, the control qubit 437 is teleported to qubit 448 in EELU 446, through the teleportation process 460 shown in the dotted rectangle. This involves a CNOT gate operation between qubit 437 and qubit 450, followed by a Hadamard gate 452 applied to qubit 437. Then, these two qubits 437 and 450 are measured in the computational basis (in |0> and |1>). Based on the outcome of these two measurements, a single qubit Pauli gate of either X 456 and/or Z 458 is applied to the qubit 418. When these operations are completed, qubit 448 assumes the exact state of qubit 437 before the teleportation process. Then, qubit 448 can be used as the control qubit to operate the circuit V 434 to the input qubits 440. A parallel operation may be performed in this case, for example, as a controlled-W operation 435 involving qubits only in EELU 446 (control qubit 439 and the input qubits 440) can be executed while the controlled-U operation 432 is executed in EELU 444.

Although the example circuit shown in FIG. 4E involves a teleported qubit 437 that is used as a "control" qubit 448 in controlled-U 432 and controlled-V 434 operations, the teleported qubit can be used for any function in a portion of a quantum circuit that spans the two or more EELUs.

Figure 4F:
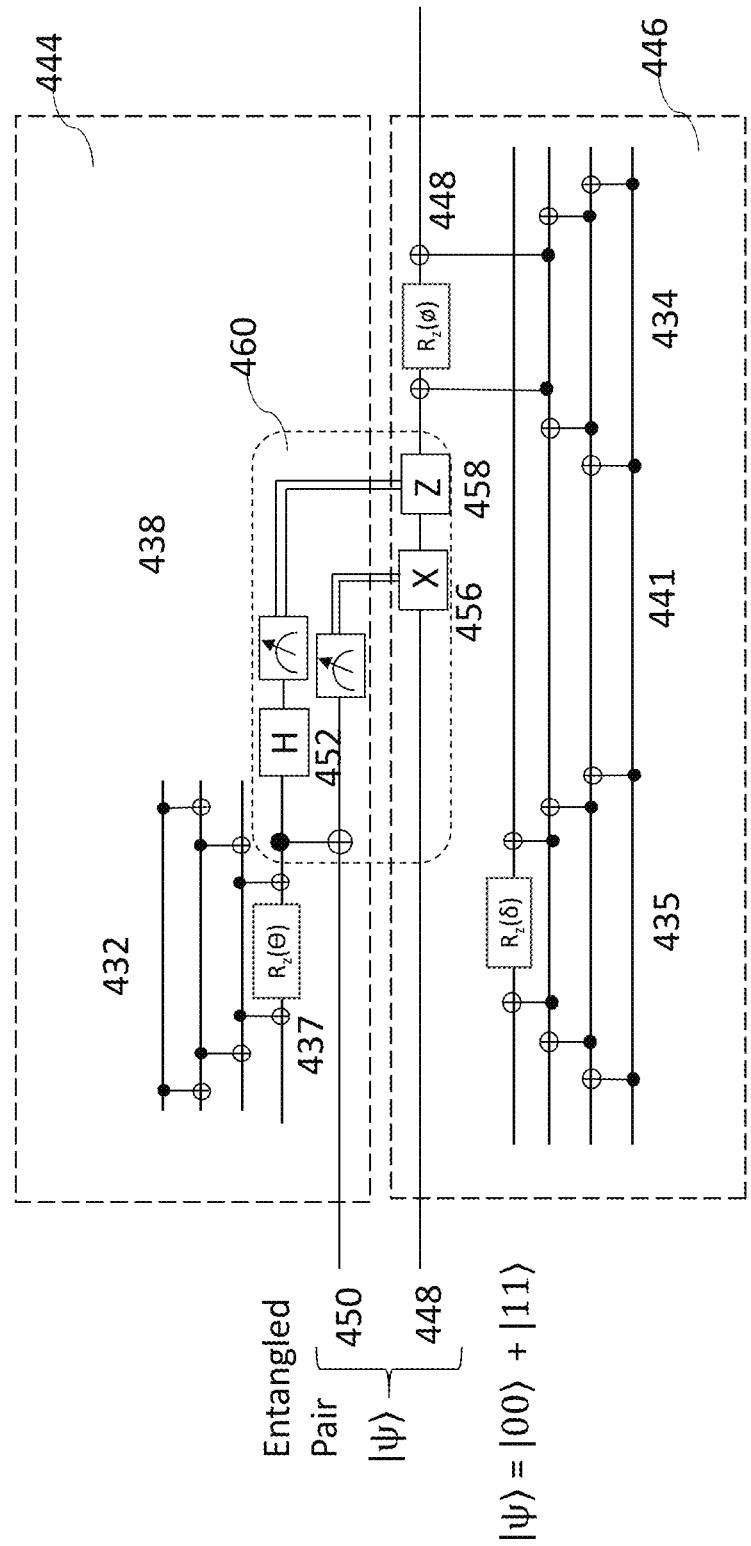
FIG. 4F shows an example processing flow by which at least portions of the method for optimizing a quantum circuit are implemented, in accordance with at least some embodiments described herein.

FIG. 4F illustrates an example of distributing quantum chemistry circuits over two EELUs, that share a common qubit. FIG. 4F shows a detailed illustration of the circuit illustrated in FIG. 4E and described in detail in the description accompanying FIG. 4E. The last qubit 437 of the upper circuit 432 is teleported to the lower circuit 434, and used, for example, in the final group of ($e^{iH_n t/n}$) in the simulation of the Trotter term.

Gate scheduling is a process by which the sequence of quantum logic gates that constitute the quantum computation process, for example, for a chemistry calculation, is applied to the qubits once they are placed onto the physical qubits in the quantum computer hardware. The circuits shown in FIGS. 3A, 3B, 4B, 4D, 4E and 4F are examples of scheduling of gates on qubits that are assigned or mapped to represent the electron populations for molecular orbits.

Further optimization of quantum resources and optimization of quantum circuit generated using optimized or minimized quantum resources may be performed in series and iteratively until a specific performance target, e.g., predefined maximum tolerance threshold or tolerance limit for the error, or minimum gate count, is achieved.

Figure 5:
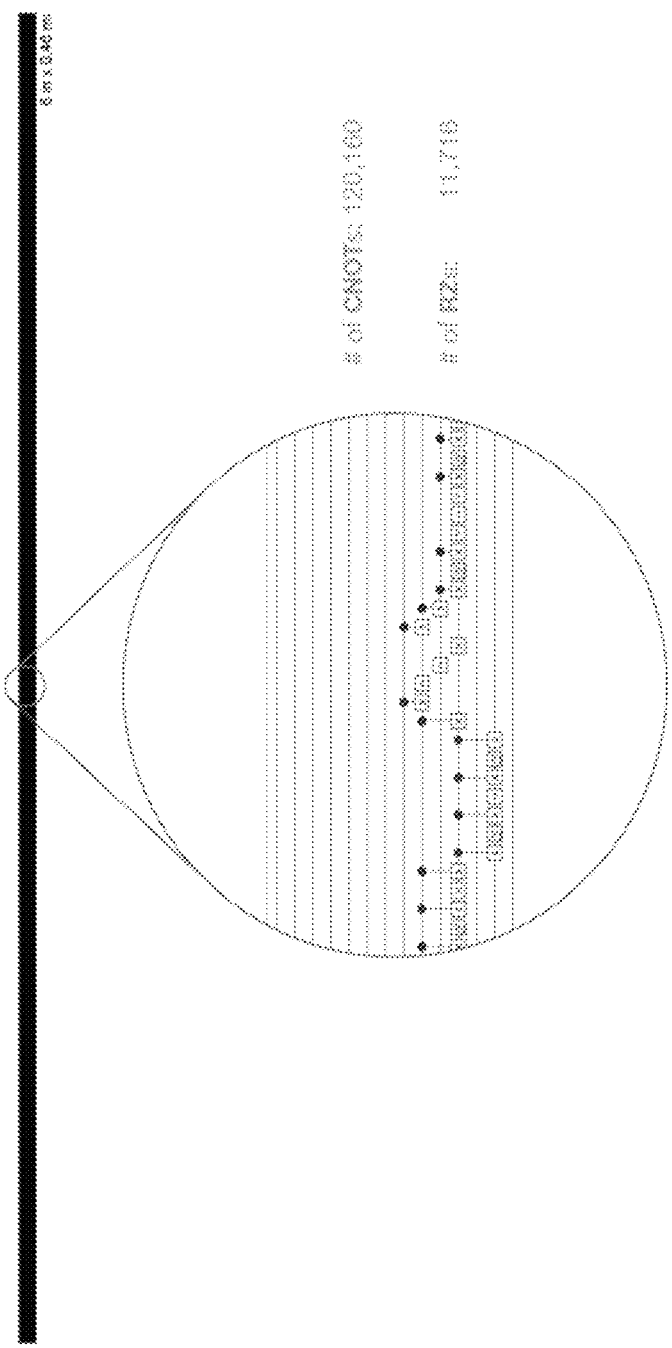
FIG. 5 shows a sample circuit created by at least portions of the different embodiments of the method for optimizing a quantum circuit, in accordance with at least some embodiments described herein.

A sample circuit using native approach with no merging, no re-embedding and no sorting is illustrated in FIG. 5. As configured, this example circuit requires 120,160 CNOT gates and 11,716 $R_Z(\theta)$ gates. The table below shows an example of the reduction of the number of gates when various circuit optimization techniques are applied to this circuit. It also reduces the number of Hadamard gates and Phase (S) gates used in the circuit. More improvements can be obtained by further optimizing the circuit.

Figure 6:
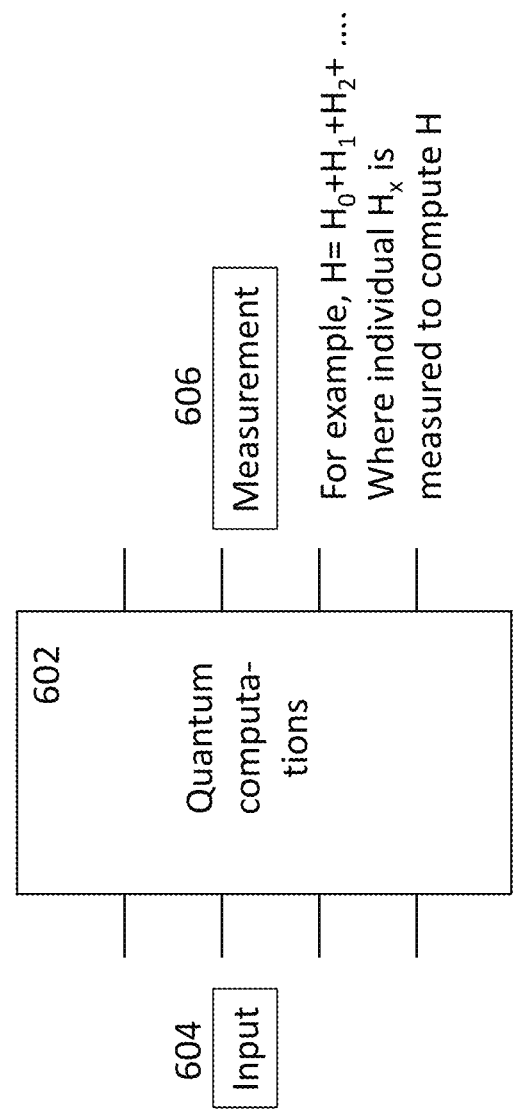
FIG. 6 Illustrates an example quantum computing system used to provide quantum state measurements for a chemical entity chose for which the quantum circuit is optimized using method and system for optimization of quantum circuit according to one or more embodiments described herein.

FIG. 6 illustrates a quantum computing system used to provide quantum state measurements for a chemical entity chosen for which the quantum circuit is optimized using method and system for optimization of quantum circuit according to one or more embodiments described herein. For example, variational quantum eigensolver (VQE) method, where a trial function for the quantum state (also known as the ansatz state) is prepared using the quantum circuit 602 utilizing the Trotter-like approach with a set of variational parameters. Once the state is prepared, it is used to estimate the expectation value of the energy (Hamiltonian). In this method, a minimum in the energy is sought by changing the variational parameters, and preparing new trial states utilizing these updated parameters. The total Hamiltonian is estimated by measuring the expectation values 606 corresponding to each term that constitutes the overall Hamiltonian. Since a Hamiltonian for a chemical entity includes a combination of Hamiltonian terms, the measurements are to be carried out in series, resulting in a number of iterations to measure individual terms in the Hamiltonian. One way to save quantum cost is to measure expectation value of more than one terms simultaneously. For example, for a quantum state with two qubits, the expectation values for the operators ⟨IZ⟨, ⟩ZI⟩ and ⟨ZZ⟩ can all be measured simultaneously from preparation of one trial function.

Figure 7:
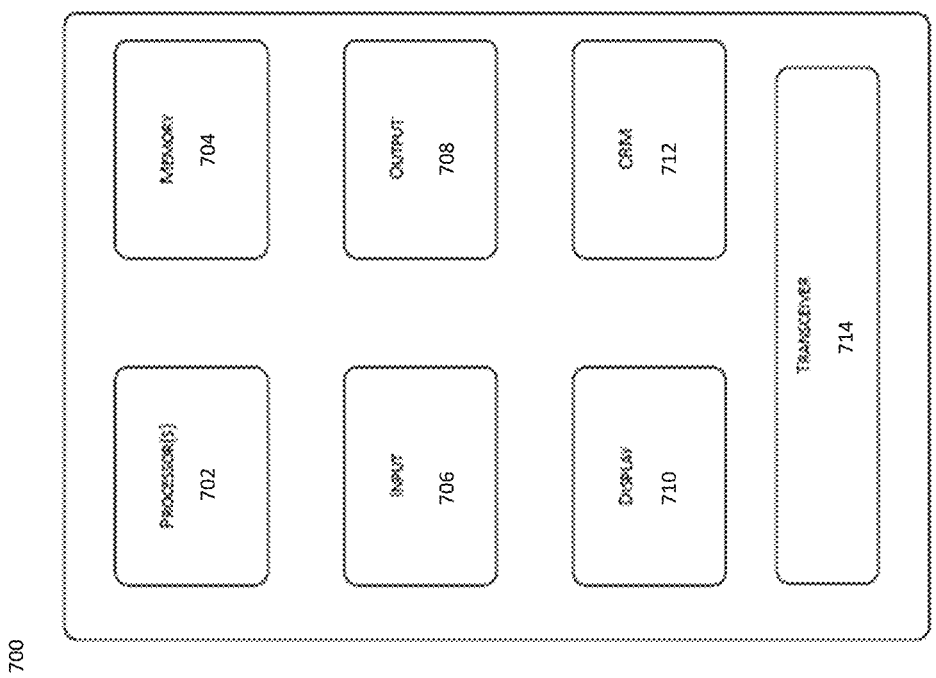
FIG. 7 shows an example classical computing system including an example computing embodiment, in which any of the processes and sub-processes for optimization of quantum circuits may be implemented as computer-readable instructions stored on a computer-readable medium.

In an embodiment, a classical computing system for optimizing a quantum circuit for simulation of the quantum system for the chemical entity is disclosed as illustrated in FIG. 7 and described in detail the description accompanying FIG. 7. The system for optimizing a quantum circuit comprising at least one processor and a memory wherein the memory stores executable instructions for optimizing a quantum circuit that, upon execution by the processor, cause the processor to perform functions including receiving one or more parameters for simulation of evolution of at least one quantum state of a chemical entity to be simulated; generating a quantum circuit for simulation of evolution of the at least one quantum state of the chemical entity; performing one or more operations to minimize quantum resources or qubits to be used for the generated quantum circuit based on the one or more parameters; and placing quantum resources among one or more elementary logical units (ELUs) based on any one or more of: frequency of occurrence of the quantum resources in the generated quantum circuit, order of occurrence of the quantum resources in the generated quantum circuit, connectivity parameters between one or more quantum resources, efficiency of gates between specific quantum resources, quality of gates between specific quantum resources or a combination thereof.

The system after receiving one or more parameters for simulation of evolution of at least one quantum state of a chemical entity to be simulated, derives a time evolution operator e't for the chemical entity; converts the derived

| Native Approach: No merging, no re-embedding, no sorting | Merge only Approach: Merging but no re-embedding or sorting | Greedy Approach: Merging, re-embedding (first order mode) and sorting |
| --- | --- | --- |
| # of controlled quantum logic gates (CNOT): 120,160 | # of controlled quantum logic gates (CNOT): 108,802 | # of controlled quantum logic gates (CNOT): 30,558 |
| # of $R_Z(\theta)$ gates: 11,716 | # of $R_Z(\theta)$ gates: 10,319 | # of $R_Z(\theta)$ gates: 10,319 |
| # of Hadamard (H) gates: 86,380 | # of Hadamard (H) gates: 76,812 | # of Hadamard (H) gates: 14,380 |
| # of Phase (S) gates: 42,048 | # of Phase (S) gates: 38,760 | # of Phase (S) gates: 6,864 | evolution operator to an evolution operator for a quantum computer to be used for simulation of the evolution of the at least one quantum state according to the evolution operator and the one or more parameters and generates a quantum circuit for simulation of the quantum system for the chemical entity, which is optimized by performing one or more operations to minimize quantum resources or qubits to be used for the generated quantum circuit based on the one or more parameters; and placing quantum resources among one or more elementary logical units (ELUs) based on any one or more of: frequency of occurrence of the quantum resources in the generated quantum circuit, order of occurrence of the quantum resources in the generated quantum circuit, connectivity parameters between one or more quantum resources, efficiency of gates between specific quantum resources, quality of gates between specific quantum resources or a combination thereof as described herein. Further optimization of quantum resources and optimization of quantum circuit generated using optimized or minimized quantum resources may be performed in series and iteratively until a specific performance target, e.g., pre-defined maximum tolerance threshold or tolerance limit for the error, or minimum gate count, is achieved. FIG. 7 illustrates one or more embodiments of the system used for optimizing a quantum circuit for simulation of the quantum system for the chemical entity using the method depicted in FIGS. 2A, 2B, 3A, 3B, 4A, 4B, 4C, 4D, 4E and 4F.

Once the quantum resources are optimized, and the quantum circuit optimized to use parallel processing and gate scheduling, the resulting optimized quantum circuit may be further optimized by using a number of iterations, also known as heuristic optimization, and the results obtained via quantum circuit are compared to the theoretical results and error tolerance. This optimization is described in detail in commonly-owned, co-pending U.S. application Ser. No. 16/164,586, "AUTOMATED OPTIMIZATION OF LARGE-SCALE QUANTUM CIRCUITS WITH CONTINUOUS PARAMETERS".

FIG. 7 shows an example system and an illustrative computing embodiment, in which any of the processes and sub-processes of quantum computation may be implemented as computer-readable instructions stored on a computer-readable medium. The computer-readable instructions may, for example, be executed by a processor of a device, as referenced herein, having a network element and/or any other device corresponding thereto, particularly as applicable to the applications and/or programs described above for quantum circuit optimization.

In an embodiment, a computer-readable medium storing executable instructions for optimizing a quantum circuit that, upon execution, cause a digital computing processor to perform functions including receiving one or more parameters for simulation of evolution of at least one quantum state of a chemical entity to be simulated; generating a quantum circuit for simulation of evolution of the at least one quantum state of the chemical entity; performing one or more operations to minimize quantum resources to be used for the generated quantum circuit based on the one or more parameters; and placing quantum resources among one or more elementary logical units (ELUs) based on any one or more of: frequency of occurrence of the quantum resources in the generated quantum circuit, order of occurrence of the quantum resources in the generated quantum circuit, connectivity parameters between one or more quantum resources, efficiency of gates between specific quantum resources, quality of gates between specific quantum resources or a combination thereof.

In a very basic configuration, a computing device or a system 700 may typically include, at least, one or more processors 702, a system memory 704, one or more input components 706, one or more output components 708, a display component 710, a computer-readable medium 712, and a transceiver 714.

Processor 702 may refer to, e.g., a microprocessor, a microcontroller, a digital signal processor, or any combination thereof.

Memory 704 may refer to, e.g., a volatile memory, non-volatile memory, or any combination thereof. Memory 704 may store, therein, operating system 705, an application, and/or program data. That is, memory 704 may store executable instructions to implement any of the functions or operations described above and, therefore, memory 704 may be regarded as a computer-readable medium.

Input component 706 may refer to a built-in or communicatively coupled keyboard, touch screen, or telecommunication device. Alternatively, input component 706 may include a microphone that is configured, in cooperation with a voice-recognition program that may be stored in memory 704, to receive voice commands from a user of computing device 700. Further, input component 706, if not built-in to computing device 700, may be communicatively coupled thereto via short-range communication protocols including, but not limitation, radio frequency or Bluetooth.

Output component 708 may refer to a component or module, built-in or removable from computing device 700, that is configured to output commands and data to an external device.

Display component 710 may refer to, e.g., a solid state display that may have touch input capabilities. That is, display component 710 may include capabilities that may be shared with or replace those of input component 706.

Computer-readable medium 712 may refer to a separable machine readable medium that is configured to store one or more programs that embody any of the functions or operations described above. That is, computer-readable medium 712, which may be received into or otherwise connected to a drive component of computing device 700, may store executable instructions to implement any of the functions or operations described above. These instructions may be complimentary or otherwise independent of those stored by memory 704.

Transceiver 714 may refer to a network communication link for computing device 700, configured as a wired network or direct-wired connection. Alternatively, transceiver 714 may be configured as a wireless connection, e.g., radio frequency (RF), infrared, Bluetooth, and other wireless protocols.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

We claim:

1. A computer-readable medium storing executable instructions for optimizing a quantum circuit that, upon execution, cause a digital computing processor to perform functions comprising:

receiving one or more parameters for simulation of evolution of at least one quantum state of a chemical entity to be simulated;

generating a quantum circuit for simulation of evolution of the at least one quantum state of the chemical entity;

performing one or more operations to minimize quantum resources to be used for the generated quantum circuit based on the one or more parameters; and placing quantum resources among one or more elementary logical units (ELUs) based on any one or more of: frequency of occurrence of the quantum resources in the generated quantum circuit, order of occurrence of the quantum resources in the generated quantum circuit, connectivity parameters between one or more quantum resources, efficiency of gates between specific quantum resources, quality of gates between specific quantum resources or a combination thereof, wherein the one or more elementary logical units (ELUs) are part of an ion-trap quantum computer.

2. The computer-readable medium of claim 1, wherein the chemical entity includes any one or more of: atoms, molecules, ions and subatomic particles, wherein the subatomic particles are free, bound or localized.

3. The computer-readable medium of claim 1, wherein generating a quantum circuit for simulation of evolution of the at least one quantum state of the chemical entity comprises:

deriving evolution operator for the chemical entity to be utilized for the simulation using a quantum computer, wherein deriving evolution operator for the chemical entity further comprises:

deriving fermionic Hamiltonian for the chemical entity, and transforming fermionic Hamiltonian to a qubit Hamiltonian using one or more transformation algorithms, wherein the one or more transformation algorithm comprises any one or more of: Jordan-Wigner transformation, Parity transformation and Bravyi-Kitaev transformation.

4. The computer-readable medium of claim 1, wherein the one or more operations to minimize quantum resources include any one or more of term merging, re-embedding quantum resources and merge-sorting.

5. The computer-readable medium of claim 1, wherein the one or more parameters for simulation of evolution of at least one quantum state of a chemical entity to be simulated include any one or more of: atomic information for the chemical entity, error tolerance for the quantum circuit, maximum number of gates permitted for the quantum circuit, maximum number of qubits permitted for the quantum circuit, and maximum duration of time allowed for the simulation.

6. The computer-readable medium of claim 1, wherein optimizing the generated quantum circuit based on the one or more parameters further comprises any one or more of: gate scheduling and parallel processing of quantum computations.

7. The computer-readable medium of claim 6, wherein the gate scheduling for quantum computations is achieved by connecting one or more quantum resources from different ELUs, wherein the quantum resources are connected by a qubit communication bus including shuttling of the quantum resources.

8. The computer-readable medium of claim 6, wherein the gate scheduling and parallel processing of quantum computations is achieved by connecting one or more quantum resources from different extended elementary logical units (EELUs) via optical cross connect to generate at least one entangled ion pair between a pair of EELUs.

9. The computer-readable medium of claim 8, wherein the number of quantum resources in each ELU, the number of ELUs in each EELU and the number of EELUs used in the computations can be dynamically varied over the duration of the computation.

10. The computer-readable medium of claim 1, wherein the one or more ELUs are formed by jump-type implementation or step-type implementation of the Hamiltonian evolution.

11. The computer-readable medium of claim 8, wherein the extended EELUs are part of the ion-trap quantum computer.

12. The computer-readable medium of claim 1, wherein one or more global gates are used to further minimize quantum resources to be used for the generated quantum circuit based on the one or more parameters.

13. The computer-readable medium of claim 12, wherein the one or more global gates to further minimize quantum resources are provided by an ion-trap quantum computer.

14. A computer-implemented method for optimizing a quantum circuit comprising:

receiving one or more parameters for simulation of evolution of at least one quantum state of a chemical entity to be simulated;

generating a quantum circuit for simulation of evolution of the at least one quantum state of the chemical entity;

performing one or more operations to minimize quantum resources to be used for the generated quantum circuit based on the one or more parameters; and mapping quantum resources among one or more elementary logical units (ELUs) based on any one or more of: frequency of occurrence of the quantum resources in the generated quantum circuit, order of occurrence of the quantum resources in the generated quantum circuit, connectivity parameters between one or more quantum resources, efficiency of gates between specific quantum resources, quality of gates between specific quantum resources or a combination thereof, wherein the one or more elementary logical units (ELUs) are part of an ion-trap quantum computer.

15. The computer-implemented method of claim 14, wherein the chemical entity includes any one or more of: atoms, molecules, ions and subatomic particles, wherein the subatomic particles are free, bound or localized.

16. The computer-implemented method of claim 14, wherein generating a quantum circuit for simulation of evolution of the at least one quantum state of the chemical entity comprises:

deriving evolution operator for the chemical entity to be utilized for the simulation using a quantum computer, wherein deriving evolution operator for the chemical entity further comprises:

deriving fermionic Hamiltonian for the chemical entity, and transforming fermionic Hamiltonian to a qubit Hamiltonian using one or more transformation algorithms, wherein the one or more transformation algorithm comprises any one or more of: Jordan-Wigner transformation, Parity transformation and Bravyi-Kitaev transformation.

17. The computer-implemented method of claim 14, wherein the one or more operations to minimize quantum resources include any one or more of term merging, re-embedding quantum resources and merge-sorting.

18. The computer-implemented method of claim 14, wherein the one or more parameters for minimizing quantum resources to be used for the generated quantum circuit include any one or more of: atomic information for the chemical entity, error tolerance for the quantum circuit, maximum number of gates permitted for the quantum circuit, maximum number of qubits permitted for the quantum circuit, and maximum duration of time allowed for the simulation.

19. The computer-implemented method of claim 14, wherein optimizing the generated quantum circuit based on the one or more parameters further comprises any one or more of: gate scheduling and parallel processing of quantum computations.

20. The computer-implemented method of claim 19, wherein the gate scheduling for quantum computations is achieved by connecting one or more quantum resources from different ELUs, wherein the quantum resources are connected by a qubit communication bus including shuttling of the quantum resources.

21. The computer-implemented method of claim 19, wherein the gate scheduling and parallel processing of quantum computations is achieved by connecting one or more quantum resources from different extended elementary logical units (EELUs) via optical cross connect to generate at least one entangled ion pair between a pair of EELUs.

22. The computer-implemented method of claim 21, wherein the number of quantum resources in each ELU, the number of ELUs in each EELU and the number of EELUs used in the computations can be varied over the duration of the computation.

23. The computer-implemented method of claim 14, wherein the one or more ELUs are formed by jump-type implementation or step-type implementation of the Hamiltonian evolution.

24. The computer-implemented method of claim 21, wherein the extended EELUs are part of the ion-trap quantum computer.

25. The computer-implemented method of claim 14, wherein one or more global gates are used to further minimize quantum resources to be used for the generated quantum circuit based on the one or more parameters.

26. The computer-implemented method of claim 25, wherein the one or more global gates to further minimize quantum resources are provided by an ion-trap quantum.

27. A system for optimizing a quantum circuit comprising at least one processor and a memory wherein the memory stores executable instructions for optimizing a quantum circuit that, upon execution by the processor, cause the processor to perform functions comprising:
receiving one or more parameters for simulation of evolution of at least one quantum state of a chemical entity to be simulated;
generating a quantum circuit for simulation of evolution of the at least one quantum state of the chemical entity;
performing one or more operations to minimize quantum resources to be used for the generated quantum circuit based on the one or more parameters; and
placing quantum resources among one or more elementary logical units (ELUs) based on any one or more of: frequency of occurrence of the quantum resources in the generated quantum circuit, order of occurrence of the quantum resources in the generated quantum circuit, connectivity parameters between one or more quantum resources, efficiency of gates between specific quantum resources, quality of gates between specific quantum resources or a combination thereof,
wherein the one or more elementary logical units (ELUs) are part of an ion-trap quantum computer.

28. The system of claim 27, wherein the chemical entity includes any one or more of: atoms, molecules, ions and subatomic particles, wherein the subatomic particles are free, bound or localized.

29. The system of claim 27, wherein generating a quantum circuit for simulation of evolution of the at least one quantum state of the chemical entity comprises:
deriving evolution operator for the chemical entity to be utilized for the simulation using a quantum computer, wherein deriving evolution operator for the chemical entity further comprises:
deriving fermionic Hamiltonian for the chemical entity, and
transforming fermionic Hamiltonian to a qubit Hamiltonian using one or more transformation algorithms, wherein the one or more transformation algorithm comprises any one or more of: Jordan-Wigner transformation, Parity transformation and Bravyi-Kitaev transformation.

30. The system of claim 27, wherein the one or more operations to minimize quantum resources include any one or more of term merging, re-embedding quantum resources and merge-sorting.

31. The system of claim 27, wherein the one or more parameters for minimizing quantum resources to be used for the generated quantum circuit include any one or more of: atomic information for the chemical entity, error tolerance for the quantum circuit, maximum number of gates permitted for the quantum circuit, maximum number of qubits permitted for the quantum circuit, and maximum duration of time allowed for the simulation.

32. The system of claim 27, wherein optimizing the generated quantum circuit based on the one or more parameters further comprises any one or more of: gate scheduling and parallel processing of quantum computations.

33. The system of claim 32, wherein the gate scheduling for quantum computations is achieved by connecting one or more quantum resources from different ELUs, wherein the quantum resources are connected by a qubit communication bus including shuttling of the quantum resources.

34. The system of claim 32, wherein the gate scheduling and parallel processing of quantum computations is achieved by connecting one or more quantum resources from different extended elementary logical units (EELUs) via optical cross connect to generate at least one entangled ion pair between a pair of EELUs.

35. The system of claim 34, wherein the number of quantum resources in each ELU, the number of ELUs in each EELU and the number of EELUs used in the computations can be varied over the duration of the computation.

36. The system of claim 27, wherein the one or more ELUs are formed by jump-type implementation or step-type implementation of the Hamiltonian evolution.

37. The system of claim 34, wherein the extended EELUs are part of the ion-trap quantum computer.

38. The system of claim 27, wherein one or more global gates are used to further minimize quantum resources to be used for the generated quantum circuit based on the one or more parameters.

39. The system of claim 38, wherein the one or more global gates to further minimize quantum resources are provided by an ion-trap quantum computer.

* * * * *